United States Patent [19]

Fozard et al.

[11] Patent Number: 4,486,441
[45] Date of Patent: Dec. 4, 1984

[54] PSEUDOTROPYL HALOGENO-BENZOATES AND THEIR USE IN MIGRAINE TREATMENT

[75] Inventors: John R. Fozard, Strasbourg-Elsau; Maurice W. Gittos, Illkirch-Graffenstaden, both of France

[73] Assignee: Merrell Toraude Et Compagnie, Strasbourg, France

[21] Appl. No.: 447,855

[22] Filed: Dec. 8, 1982

[51] Int. Cl.³ .................. C07D 451/12; A61K 31/46
[52] U.S. Cl. ..................................... 424/265; 546/127
[58] Field of Search .......................... 546/127; 424/265

[56] References Cited

PUBLICATIONS

Hamor, Chemical Abstracts, vol. 86, No. 13, Abst. No. 90,095n, Mar. 28, 1977.
Wallace et al., Chemical Abstracts, vol. 89, No. 5, Abst. 43,870p, Jul. 31, 1978.

Primary Examiner—Alan L. Rotman
Attorney, Agent, or Firm—William J. Stein; Raymond A. McDonald; Gary D. Street

[57] ABSTRACT

Migraine is treated with a novel pseudotropyl benzoate derivative of the following general Formula I:

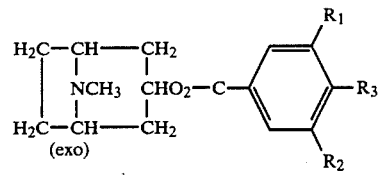

wherein:
$R_1$ represents halogen, preferably chlorine;
$R_2$ represents hydrogen or halogen, preferably chlorine; and
$R_3$ represents hydrogen or halogen, preferably chlorine, provided that $R_3$ is hydrogen when $R_2$ is hydrogen.

7 Claims, No Drawings

PSEUDOTROPYL HALOGENO-BENZOATES AND THEIR USE IN MIGRAINE TREATMENT

FIELD OF THE INVENTION

The invention relates to the treatment of migraine with certain novel pseudotropyl halogenobenzoates and provides pharmaceutical compositions comprising said compounds, methods of treating migraine using said compounds, said compounds for use in treating migraine, and said novel compounds per se.

BACKGROUND OF THE INVENTION

Acute attacks of migraine are usually treated with a peripheral vasoconstrictor, such as ergotamine, which may be co-administered with caffeine, and dihydroergotamine; an antipyretic analgesic, such as acetylsalicylic acid or p-acetylaminophenol; and/or an antiemetic such as cyclizine, metoclopramide and thiethylperazine. It has also been reported (J. B. Hughes; Med. J. Aust. 2, No. 17, 580, 1977) that immediate relief of acute migraine attack can be obtained by slow intravenous injection of metoclopramide (10 mg).

It is believed that 5-hydroxytryptamine (5-HT) is the naturally occuring substance most likely to play a role in the pathophysiology of migraine. Increased amounts of 5-HT and its metabolite 5-hydroxyindoleacetic acid are excreted in the urine during most attacks. Further, plasma and platelet 5-HT concentrations fall rapidly at the onset of an attack and remain low whilst the headache persists. Moreover, attacks of migraine have been clearly associated with periods of thrombocytopaenia in certain patients. It has been proposed that compounds which block the activity of 5-HT would be of use in the treatment of migraine (J. R. Fozard, International Headache Congress 1980) reported in Advances in Neurology, Vol 33, Raven Press, New York 1982).

The known migraine prophylactic drugs methysergide, propranolol, amitriptyline, and chlorpromazine have widely different pharmacological activities but are all 5-HT D-receptor antagonists at the doses used clinically for the treatment of migraine. Metoclopramide is a potent 5-HT M-receptor antagonist and it has been proposed (J. R. Fozard supra) that blockade of the M-receptor present on afferent sensory neurones affords symptomatic relief in an acute migraine attack.

The potency as 5-HT M-receptor antagonists of (−) cocaine and some related compounds, including pseudotropyl benzoate (i.e. benzoylpseudotropine), has been reported (J. R. Fozard et al, Eur. J. Pharmacol., 59(1979), 195–210) but, with the exceptions of nor(−)cocaine and benzoyltropine, none are as potent as metoclopramide. The $pA_2$ values reported for pseudotropyl benzoate, nor(−)cocaine and benzoyltropine are 7.0, 7.7 and 7.2 respectively whilst the $pA_2$ 5-HT value determined for metoclopramide by the same procedure is 7.2 (J. R. Fozard et al. Eur. J. Pharmacol., 49(1978), 109–112).

It has been reported in U.S. patent application No. 386,562 filed June 9th 1982 (as yet unpublished) that substitution of tropylbenzoate (i.e. benzoyltropine) with alkyl, alkoxy or halogen in the 3, 4 and 5, or 3, 4 and 5 positions of the benzene ring surprisingly substantially enhances its potency as a 5-HT M-receptor antagonist. Tests conducted with pseudotropyl-3,5-dimethoxybenzoate ($pA_2$ 6.6) and pseudotropyl-3,4,5-trimethoxybenzoate ($pA_2$ 5.7) indicated that corresponding substitutions in the benzene ring of pseudotropyl benzoate would reduce its potency as a 5-HT M-receptor antagonist.

The present invention comprehends novel pseudotropyl benzoate derivatives having substitution by halogen in the 3, 3 and 5, or 3,4, and 5 positions of the benzene ring, which derivatives have enhanced potency as 5-HT M-receptor antagonists.

SUMMARY OF THE INVENTION

According to a first aspect of the invention, there are provided pseudotropyl benzoate derivatives of the following general Formula I:

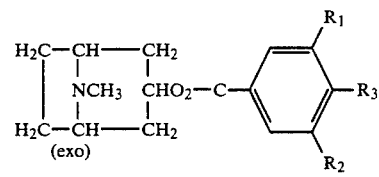

wherein:
$R_1$ represents halogen;
$R_2$ represents hydrogen or halogen; and
$R_3$ represents hydrogen or halogen provided that $R_3$ is hydrogen when $R_2$ is hydrogen,
or a pharmaceutically acceptable salt thereof.

According to a second aspect of the invention there are provided pharmaceutical compositions in unit dose form for the effective relief of migraine comprising a compound of general Formula I in admixture or otherwise associated with a pharmaceutically acceptable diluent or carrier and containing 0.5 to 100 mg per unit dose. Usually, said compositions will contain 1 to 50 mg, especially 3 to 30 mg, per unit dose.

According to a third aspect of the invention, there are provided compounds of Formula I for use in the treatment of migraine and other vascular headaches.

According to a fourth aspect of the invention, there is provided a method of treating migraine which comprises administering to a patient suffering migraine, an effective migraine-relieving amount of a compound of Formula I. Said amount usually will be in the range 0.01 mg/kg to 10 mg/kg, especially 0.03 mg/kg to 3.0 mg/kg. It is also contemplated that the compounds of Formula I can be used in the prophylaxis of migraine by administering to a patient at risk of migraine an effective migraine-prophylatic amount of the compound.

DETAILED DESCRIPTION OF THE INVENTION

The compounds of general Formula I have the benzoyloxy moiety substituted in that $R_1$ represents halogen; $R_2$ can represent halogen instead of hydrogen; and $R_3$ is hydrogen except when $R_2$ is halogen, in which case $R_3$ can represent halogen instead of hydrogen.

The halogens which can be represented by $R_1$, $R_2$ and $R_3$ are bromine, chlorine, fluorine and iodine with bromine, fluorine and, especially, chlorine being preferred.

One preferred compound of Formula I is that in which $R_1$ represents chlorine, $R_2$ represents hydrogen, and $R_3$ represents hydrogen, i.e. pseudotropyl-3-chlorobenzoate.

Another preferred compound of Formula I is that in which $R_1$ and $R_2$ are the same and each represents chlorine, and $R_3$ represents hydrogen, i.e. pseudotropyl-3,5-dichlorobenzoate.

Yet another preferred compound of Formula I is that in which $R_1$, $R_2$ and $R_3$ are all the same and each represents chlorine, i.e. pseudotropyl-3,4,5-trichlorobenzoate.

In addition to the preferred chloro compounds specified above, the following are compounds of Formula I:
pseudotropyl 3-bromobenzoate;
pseudotropyl 3-iodobenzoate;
pseudotropyl 3-fluorobenzoate;
pseudotropyl 3,5-dibromobenzoate;
pseudotropyl 3,5-diiodobenzoate;
pseudotropyl 3,5-difluorobenzoate;
pseudotropyl 3,4,5-tribromobenzoate;
pseudotropyl 3,4,5-triiodobenzoate;
pseudotropyl 3,4,5-trifluorobenzoate.

The compounds of Formula I block the M-receptors for 5-hydroxytryptamine (5-HT) on afferent sensory neurones, certain of which subserve the transmission of pain. As explained above, the blocking of such M-receptors is believed to be a mechanism by which the symptoms of migraine can be relieved. Accordingly, the compounds of Formula I are useful in the treatment of migraine when administered in amounts sufficient to effectively block the said M-receptors.

The activity of the compounds against 5-HT can be assessed by determining their $pA_2$ values in the isolated rabbit heart as described by Fozard et at Europ. J. Pharmacol. 59, 195–210 (1979). In the method described the molar concentration of antagonist which reduces the effects of twice the ED50 of 5-HT to that of the ED50 in the absence of antagonist is determined. The $pA_2$ value is the negative logarithm of said molar concentrations. In general terms, the higher the $pA_2$ value the more potent is the compound.

The activity of the compounds against 5-HT can be assessed in vivo by measurement of the effect of the compound on the Von Bezold-Jarisch Reflex induced by 5-HT injected intravenously into the rat (see Paintal A.S., Physiol. Rev. 53 159–227, 1973). The transient cardiac slowing arises from an increased efferent vagus activity arising from stimulation by 5-HT of sensory afferent fibres in and around the heart.

The compounds of Formula I are believed to be highly selective in their action against 5-HT M-receptor. Their potency against other 5-HT recepors and other spasmogens, in particular oxytocin, acetylcholine, histamine and calcium, is believed to be at least two orders lower than that against 5-HT M-receptors. Accordingly, their use in the treatment of migraine should be without any side effects.

The compounds of Formula I can be administered in various manners to achieve the desired effect. The compounds can be administered alone or in the form of pharmaceutical preparations to the patient being treated either orally or parenterally, for example, subcutaneously or intravenously. The amount of compound administered will vary and can be any effective migraine-relieving amount. Depending upon the patient and the mode of administration, the quantity of compound administered may vary over a wide range to provide from about 0.01 mg/kg to about 10 mg/kg, usually 0.03 to 3.0 mg/kg, of body weight of the patient per dose. Unit doses of these compounds can contain, for example, from about 0.5 mg to 100 mg, usually 1 to 50 mg and preferably 3 to 30 mg, of the compound and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making those formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

The pseudotropyl benzoate derivatives of Formula I can be used in migraine therapy with antimigraine drugs having different modes of action. Such drugs include those used prophylactically, such as barbiturates; diazepam, chlorpromazine, amitriptyline, propranolol, methysergide, pizotifen, cyproheptadine, dihydroergotamine, and clonidine, and those used in the acute attack, such as vasoconstrictor agents, e.g. ergotamine and dihydroergotamine, analgaesic/antiinflammatory agents, e.g. aspirin, paracetamol and indomethacin, or anti-nauseants, e.g. cyclizine, metoclopramide, and triethylperazine (see Fozard, J. R. J. Pharm. Pharmacol. 27, 297–321 (1975); Saper, J. R., J. Amer. Med. Assoc. 239, 480–484 (1978); Fozard, J. R., supra.) As an example, compounds of general Formula I would be beneficial in combination with aspirin 300–1200 mg or methysergide, 2–6 mg given daily.

The compounds of general Formula I can be prepared in manner known per se from tropine and an acid halide of the following general Formula IV:

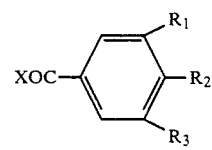

Formula IV wherein:
$R_1$, $R_2$ and $R_3$ are as defined in connection with Formula I, and X represents halogen, especially chlorine.

The reaction usually will be carried out by stirring the acid halide and pseudotropine in an aprotic solvent, preferably methylene chloride or acetonitrile, at ambient temperature. The solvent is evaporated off, usually under reduced pressure, after about 2 to 16 hours and water added to the residue, followed by aqueous base, such as sodium or potassium carbonate, which does not hydrolyse the ester, to render the aqueous product solution alkaline. Subsequently desired free base is extracted with a suitable organic solvent such as, for example, diethyl ether, ethylacetate and methylene chloride. The organic solution is then washed with water to remove excess pseudotropine and dried. The organic solvent is evaporated off and the free base recrystallized from, for example, aqueous methanol. Alternatively, the crude free base can be converted into an acid addition salt, preferably hydrochloride, by addition of an ethereal solution of the acid. The acid salt is recrystallized from, for example ethanol or isopropanol.

As mentioned previously, the compounds of Formula I can be used in the form of their pharmaceutically acceptable acid addition salts.

The pharmaceutically acceptable acid addition salts can be non-toxic addition salts with suitable acids, such as those with inorganic acids, for example hydrochloric, hydrobromic, nitric, sulfuric or phosphoric acids, or with organic acids, such as organic carboxylic acids, for example, glycollic, maleic, hydroxymaleic, malic, tartaric, citric, salicylic, o-acetyloxybenzoic, nicotinic or isonicotinic, or organic sulphonic acids, for example methane sulphonic, ethane sulphonic, 2-hydroxyethane sulphonic, toluene-p-sulphonic, or naphthalene-2-sulphonic acids.

Apart from pharmaceutically acceptable acid addition salts, other acid addition salts, such as for example, those with picric or oxalic acid, may be serve as intermediates in the purification of the compounds or in the preparation of other, for example, pharmaceutically acceptable, acid addition salts, or are useful for identification or characterisation of the bases.

An acid addition salt may be converted into the free compound according to known methods, for example, by treating it with a base, such as with a metal hydroxide or alkoxide, for example an alkali or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate; with trialkylamine; or with an anion exchange resin.

An acid addition salt may also be converted into another acid addition salt according to known methods; for example, a salt with an inorganic acid may be treated with a metal salt, for example a sodium, barium or silver salt, or an acid in a suitable diluent, in which a resulting inorganic salt is insoluble and is thus removed from the reaction medium. Acid addition salt may also be converted into another acid addition salt by treatment with an anion exchange preparation.

The invention is illustrated in the following non-limiting Examples.

EXAMPLE 1

Pseudotropyl 3,5-Dichlorobenzoate (i.e. 3,5-Dichlorobenzoic Acid Exo-8-Methyl-8-Azabicyclo[3,2,1]Oct-3-Yl Ester)

(Formula I, $R_1=R_2=Cl$, $R_3=H$)

Pseudotropine (1.41 g) and 3,5 dichlorobenzoylchloride (2.06 g) in acetonitrile (50 ml) is stirred at ambient temperature for 16 hours. The solvent is evaporated off under reduced pressure and the residue treated with water (50 ml) and saturated aqueous potassium carbonate solution (5 ml) is added. The mixture is extracted with diethylether, the ethereal solution washed several times with water, dried and evaporated. The crystalline residue is recrystallized from aqueous methanol to give pseudotropyl 3,5 dichlorobenzoate: m.p. 89° C.; $pA_2$(5-HT) 8.6.

In the following Examples relating to pharmaceutical compositions, the term "active compound" is used to indicate the compound pseudotropyl-3,5-dichlorobenzoate. This compound may be replaced in these compositions by any other compound of Formula I, for example by pseudotropyl-3,4,5-trichlorobenzoate. Adjustments in the amount of medicament may be necessary or desirable depending upon the degree of activity of the medicament as is well known in the art.

EXAMPLE 2

An illustrative composition for hard gelatin capsules is as follows:

| (a) | active compound | 5 mg |
|---|---|---|
| (b) | talc | 5 mg |
| (c) | lactose | 90 mg |

The formulation is prepared by passing the dry powders of (a) and (b) through a fine mesh screen and mixing them well. The powder is then filled into hard gelatin capsules at a net fill of 100 mg per capsule.

EXAMPLE 3

An illustrative composition for tablets is as follows:

| (a) | active compound | 5 mg |
|---|---|---|
| (b) | starch | 43 mg |
| (c) | lactose | 50 mg |
| (d) | magnesium stearate | 2 mg |

The granulation obtained upon mixing the lactose with the compound (a) and part of the starch and granulating with starch paste is dried, screened, and mixed with the magnesium stearate. The mixture is compressed into tables weighing 100 mg each.

EXAMPLE 4

An illustrative composition for an injectable suspension is the following 1 ml ampule for an intramuscular injection:

| | | Weight percent |
|---|---|---|
| (a) | active compound | 0.01 |
| (b) | polyvinylpyrrolidone | 0.5 |
| (c) | lecithin | 0.25 |
| (d) | water for injection to make | 100.0 |

The material (a)–(d) are mixed, homogenized, and filled into 1 ml ampules which are sealed and autoclaved 20 minutes at 121° C. Each ampule contains 1.0 mg per ml of compound (a).

EXAMPLE 5

| | mg/suppository |
|---|---|
| Active Compound | 5 |
| Oil of Theobroma (cocoa butter) | 995 |

The medicament is powdered and passed through a B.S. No. 100 Sieve and triturated with molten oil of theobroma at 45° C. to form a smooth suspension. The mixture is well stirred and poured into moulds each of nominal 1 G capacity, to produce suppositories.

We claim:

1. A method of treating migraine which comprises administering to a patient suffering migraine, an effective migraine-relieving amount of a pseudotropyl benzoate derivative having the formula:

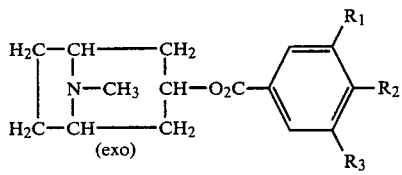

wherein:
- $R_1$ represents halogen;
- $R_2$ represents hydrogen or halogen; and
- $R_3$ represents hydrogen or halogen provided that $R_3$ is hydrogen when $R_2$ is hydrogen or a pharmaceutically acceptable salt thereof.

2. A method of prophylaxis of migraine according to claim 1 wherein the effective migraine-relieving amount is an effective migraine-prophylactic amount.

3. The method of claim 1 wherein the compound is pseudotropyl-3-chlorobenzoate or a pharmaceutically acceptable salt thereof.

4. The method of claim 1 wherein the compound pseudotropyl-3,5-dichlorobenzoate or a pharmaceutically acceptable salt thereof.

5. The method of claim 1 wherein the compound is pseudotropyl-3,4,5-trichlorobenzoate or a pharmaceutically acceptable salt thereof.

6. The method of claim 1 wherein the said compound is administered in an amount of 0.01 mg/kg to 10 mg/kg body weight.

7. The method of claim 1 wherein the said compound is administered in an amount of 0.03 mg/kg to 3.0 mg/kg body weight.

* * * * *